(12) United States Patent
Mansson et al.

(10) Patent No.: US 10,905,864 B2
(45) Date of Patent: Feb. 2, 2021

(54) LEVELLING DEVICE FOR POSITIONING OF A MEDICAL DEVICE

(71) Applicant: INNOVATION SKÅNE AB, Lund (SE)

(72) Inventors: Rose-Marie Mansson, Eslöv (SE); David Wensbo Posaric, Lund (SE)

(73) Assignee: INNOVATION SKÅNE AB, Lund (SE)

( * ) Notice: Subject to any disclaimer, the term of this patent is extended or adjusted under 35 U.S.C. 154(b) by 0 days.

(21) Appl. No.: 16/649,258

(22) PCT Filed: Oct. 29, 2018

(86) PCT No.: PCT/SE2018/051104
§ 371 (c)(1),
(2) Date: Mar. 20, 2020

(87) PCT Pub. No.: WO2019/088902
PCT Pub. Date: May 9, 2019

(65) Prior Publication Data
US 2020/0276423 A1     Sep. 3, 2020

(30) Foreign Application Priority Data
Oct. 30, 2017    (SE) ...................................... 1730296

(51) Int. Cl.
*A61M 27/00*     (2006.01)
*F16M 11/04*     (2006.01)
*A61B 5/03*      (2006.01)

(52) U.S. Cl.
CPC .......... *A61M 27/00* (2013.01); *F16M 11/046* (2013.01); *A61B 5/031* (2013.01);
(Continued)

(58) Field of Classification Search
CPC .......... A61M 27/00; A61M 2205/3331; A61M 2209/084; A61M 2210/0687; F16M 11/046; F16M 2200/00; A61B 5/031
(Continued)

(56) References Cited

U.S. PATENT DOCUMENTS 3,957,050 A * 5/1976 Hines, Jr. ............ A61M 27/006
                                                       604/118
4,669,484 A * 6/1987 Masters ................. A61B 5/021
                                                        33/367
(Continued)

FOREIGN PATENT DOCUMENTS

CN      202314546 U    7/2012
DE      10317308 A1   11/2004
(Continued)

*Primary Examiner* — Andrew J Mensh
(74) *Attorney, Agent, or Firm* — Bay State IP, LLC

(57) ABSTRACT

A levelling device for positioning of a medical device in relation to a patient is disclosed. The levelling device comprises a tube having fluid communication between a first end and a second end, wherein the first end is configured for connection to the medical device and the second end is configured for connection to the patient. The levelling device comprises a control unit connected to a sensor, wherein the sensor is configured to transmit sensor data to the control unit which is indicative of a pressure difference between the first and second end of the tube, and an actuator connected to the control unit, wherein the actuator is configured to connect to the medical device and to arrange a position of the medical device in relation to the patient in dependence on said pressure difference.

13 Claims, 2 Drawing Sheets

(52) U.S. Cl.
CPC .............. *A61M 2205/3331* (2013.01); *A61M 2209/084* (2013.01); *A61M 2210/0687* (2013.01); *F16M 2200/00* (2013.01)

(58) Field of Classification Search
USPC ........................................................ 604/540
See application file for complete search history.

(56) References Cited

U.S. PATENT DOCUMENTS

| | | | | |
|---|---|---|---|---|
| 5,280,789 | A * | 1/1994 | Potts | A61B 5/02152 33/379 |
| 5,683,357 | A * | 11/1997 | Magram | A61M 1/0021 604/8 |
| 5,752,520 | A * | 5/1998 | Bisnaire | A61B 5/031 600/485 |
| 5,836,081 | A | 11/1998 | Orosz, Jr. | |
| 6,159,160 | A * | 12/2000 | Hsei | A61M 1/0058 600/560 |
| 6,881,210 | B2 * | 4/2005 | Wilson | A61B 5/031 604/540 |
| 8,211,051 | B2 * | 7/2012 | Delaporte | A61B 5/031 604/9 |
| 9,662,478 | B2 * | 5/2017 | Browd | A61B 5/031 |
| 2007/0293847 | A1 | 12/2007 | Wilson | |
| 2011/0257631 | A1 * | 10/2011 | Murphy | G01C 15/004 604/540 |

FOREIGN PATENT DOCUMENTS

| | | |
|---|---|---|
| WO | 9944499 A1 | 9/1999 |
| WO | 2005032364 A1 | 4/2005 |

\* cited by examiner

LEVELLING DEVICE FOR POSITIONING OF A MEDICAL DEVICE

CROSS REFERENCE TO RELATED APPLICATION

This application is for entry into the U.S. National Phase under § 371 for International Application No. PCT/SE2018/051104 having an international filing date of Oct. 29, 2018, and from which priority is claimed under all applicable sections of Title 35 of the United States Code including, but not limited to, Sections 120, 363, and 365(c), and which in turn claims priority under 35 USC 119 to Sweden Patent Application No. 1730296-9 filed on Oct. 30, 2017.

TECHNICAL FIELD

The present invention generally relates to medical devices and more particularly to a levelling device for positioning of a medical device in relation to a patient and a related method.

BACKGROUND

There are several situations when accurate pressure regulation of bodily fluids is critical to a patient, as well as control of fluids delivered to the patient. A medical device such as a fluid drainage may be connected to the patient so that excess fluid may escape from the body, e.g. from the skull of the patient in case of having an excess of cerebrospinal fluid or blood from a trauma accumulating around the brain. The excess fluid or blood lead to an increase of the pressure in the skull, with the risk of causing brain damages. A fluid drainage device is thus typically connected to the skull in those situations. It is critical to maintain a certain interval of the pressure in the skull so that the fluid may readily escape as needed, while at the same time maintaining a desired pressure level of cerebrospinal fluid and/or blood in the diseased or damaged area. Previous techniques for pressure control in the mentioned case are often cumbersome, both for the care provider and the patient, and the patient's freedom of movement is often limited and typically associated with various complications. There are also issues with other medical devices adapted to be in fluid communication with the patient, such as devices adapted for delivering fluids to the patient where accurate pressure control is critical. Again, the freedom of movement of the patient may be restricted and/or the burden on the care provider can be significantly increased.

It would thus be advantageous with a levelling device for positioning of a medical device in relation to a patient that allows for avoiding more of the above-mentioned problems and compromises, including providing for facilitated control of the position of a pressure sensitive medical device in relation to a patient, and facilitated control of a fluid drainage from a patient, or infusion of a fluid to a patient.

SUMMARY

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect a levelling device for positioning of a medical device in relation to a patient is provided. The levelling device comprises a tube having fluid communication between a first end and a second end, wherein the first end is configured for connection to the medical device and the second end is configured for connection to the patient. The levelling device comprises a control unit connected to a sensor, wherein the sensor is configured to transmit sensor data to the control unit which is indicative of a pressure difference between the first and second end of the tube, and an actuator connected to the control unit, wherein the actuator is configured to connect to the medical device and to arrange a position of the medical device in relation to the patient in dependence on said pressure difference.

According to a second aspect a method of controlling the position of a medical device in relation to a patient is provided. The method comprises transmitting sensor data to a control unit which is indicative of a pressure difference between a first and second end of a tube being configured for connection to the medical device and the patient respectively, the first and second ends of the tube being in fluid communication. The method comprises controlling an actuator connected to the control unit and the medical device to arrange a position of the medical device in relation to the patient in dependence on said pressure difference.

According to a third aspect a computer program product comprising instructions which, when the program is executed by a computer, cause the computer to carry out the steps of the method according to the second aspect.

Further examples of the invention are defined in the dependent claims, wherein features for the second and third aspects of the disclosure are as for the first aspect mutatis mutandis.

Some examples of the disclosure provide for facilitated control of the position of a pressure sensitive medical device in relation to a patient.

Some examples of the disclosure provide for facilitated control of a fluid drainage from a patient or infusion of a fluid to a patient.

Some examples of the disclosure provide for facilitated and more safe control of fluid drainage from a patient's skull.

Some examples of the disclosure provide for an automatic and real-time control of the pressure in a body part of a patient such as in the patient's skull.

Some examples of the disclosure provide for an increased freedom of movement of a patient in fluid communication with a medical device.

Some examples of the disclosure provide for a more accurate and robust control of the pressure in a fluid retrieved or delivered to a body part of a patient.

Some examples of the disclosure provide for increased patient safety while reducing care resources.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the invention are capable of will be apparent and elucidated from the following description of examples of the present invention, reference being made to the accompanying drawings, in which.

DETAILED DESCRIPTION

Figure 1:
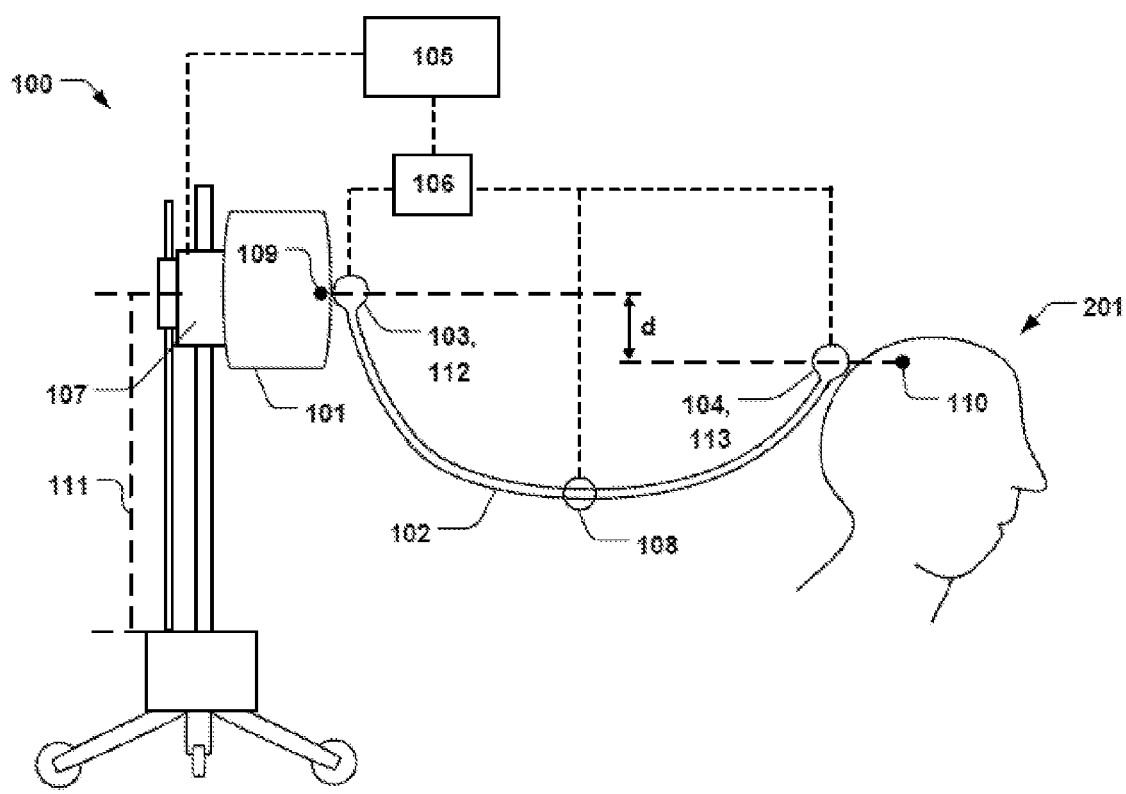
FIG. 1 is a schematic illustration of a levelling device for positioning of a medical device in relation to a patient, according to examples of the disclosure.

Specific examples of the invention will now be described with reference to the accompanying drawings. This invention may, however, be embodied in many different forms and should not be construed as limited to the examples set forth herein; rather, these examples are provided so that this disclosure will be thorough and complete, and will fully convey the scope of the invention to those skilled in the art. The terminology used in the detailed description of the examples illustrated in the accompanying drawings is not intended to be limiting of the invention. In the drawings, like numbers refer to like elements.

FIG. 1 is a schematic illustration of a levelling device 100 for positioning of a medical device 101 in relation to a patient 201. The levelling device 100 comprises a tube 102 having fluid communication between a first end 103 and a second end 104. The first end 103 is configured for connection to the medical device 101 and the second end 104 is configured for connection to the patient 201. As elucidated further below, the first end 103 may be configured to be attached to a medical device 101 by fixing the position of the first end 103 in relation to a reference point 109 of the medical device 101. It is not necessary for the first end 103 to be in fluid communication with the medical device 101, nor for the second end 104 to be in fluid communication with the patient 201. Thus, the tube 102 may be a vessel having a confined volume with fluid communication between the first 103 and second 104 end. The medical device 101 may comprise any device adapted for establishing a fluid transport from, or to, the patient 201. Thus, medical device 101 may comprise a catheter (not shown) configured to be in communication with a bodily cavity, lumen, organ etc of the patient 201 from which a fluid is to be retrieved or delivered. The position of the medical device 101 in relation to the patient 201 affects the particular pressure the fluid needs to overcome in order to be expelled from such bodily cavity— or transported to such cavity—at a desired rate. The levelling device 101 comprises a control unit 105 connected to a sensor 106. The sensor 106 is configured to transmit sensor data to the control unit 105 which is indicative of a pressure difference between the first 103 and second end 104 of the tube 102. The fluid in the tube 102 thus assumes a pressure at the first and second ends 103, 104, and the difference in pressure between the ends 103, 104, is affected by the relative positions, e.g. the relative vertical positions, thereof. The levelling device 100 comprises an actuator 107 which is connected to the control unit 105. The actuator 107 may be an electromechanical and/or hydraulic actuator configured to be connected or attached to the medical device 101. The actuator 107 is configured to arrange a position (d) of the medical device 101 in relation to the patient 201 in dependence on the aforementioned pressure difference between the first and second ends 103, 104. Hence, the control unit 105 and actuator 107 provides for adjusting the relative position (d) between the medical device 101 and the patient 201, i.e. the relative position (d) between the first and second ends 103, 104, in dependence of the detected pressure difference between the first and second ends 103, 104. The pressure difference may thus be controlled, since there is a fluid communication between the first and second ends 103, 104, and relative positions thereof are adjusted. This allows for automatic control and real-time adjustment and compensation of the pressure difference e.g. when the patient 201 moves in relation to the medical device 101. For example, the second end 104 of the tube 102 may be attached at a reference point 110 to the patient 201. The patient 201 may move from a horizontal position to an upright sitting position, i.e. upwards in the example of FIG. 1, so that the distance (d) between the second end 104 and the first end 103 being attached to the medical device 101 at a second reference point 109, decreases. This will also cause the pressure difference between the first and second ends 103, 104, to change, since the distance (d) changes. In one example, the second end 104 may be attached to a reference point 110 located at the position of a catheter being in fluid communication with a fluid-filled cavity inside the skull. The first end 103 may be attached at a reference point 109 arranged at a fluid drainage outlet, in case the medical device 101 is a fluid drainage. As the patient 201 moves upwards, so that the aforementioned distance (d) is decreased, the counter pressure that needs to be overcome by the fluid in the skull, in order to be expelled from the cavity, is reduced. The pressure in the cavity may thus become too low, as fluid can be expelled from the cavity at a higher rate when the pressure difference is lowered. The sensor 106 is thus configured to detect the decreasing pressure difference between the first and second ends 103, 104, and communicate this sensor data to the control unit 105 which may instruct the actuator 107 to move the medical device 101 and the associated drainage outlet, in this example positioned at reference point 109, further upwards (in FIG. 1) to compensate for the patient's movement and maintain a defined distance (d) that allows for the pressure difference to be kept at desired value. Likewise, if the patient in FIG. 1 decides to again assume a horizontal resting position, and lowers his/her head in relation to the medical device 101 so that distance (d) is increased, the pressure difference between the drainage outlet (i.e. first end 103 located at reference point 109) and the skull (i.e. second end 104 located at the skull at reference point 110) may become too high for the fluid to escape from the patient's skull. The sensor 106 is configured to detect the resulting change in pressure difference between the first and second ends 103, 104 (in this case the increasing pressure difference) and communicate this sensor data to the control unit 105 which instructs the actuator 107 to lower the medical device 101 to compensate for the patient's movement and keep the distance (d) at a defined value to maintain a desired pressure difference.

As described above, the levelling device 100 provides for effectively compensating the position of a medical device 101 in relation to the patient 201 as the patient 201 moves to different positions, to automatically and in real-time maintain an optimal distance (d) between the medical device 101 and the patient 201, and thereby an optimized working pressure for the medical device 101 when in fluid communication with the patient 201. Patient safety may thus be improved, while allowing for increased mobility without increasing the burden on the health care provider.

The sensor 106 may be connected to the first and second end 103, 104, of the tube 102 and may be configured to detect the pressure difference therebetween, as schematically illustrated in FIG. 1. It is conceivable however that the sensor 106 may be connected to other parts of the tube 102, such as at an intermediate position (indicated by denotation 108) as described further below, or to any other part in order to optimize the sensing of the pressure difference.

The first and second ends 103, 104, may comprise respective first and second chambers 112, 113, being in fluid communication across the tube 102. The sensor 106 may hence be configured to detect the pressure difference between the first and second chambers 112, 113.

The sensor 106 may be connected to an intermediate sensor element 108 positioned in fluid communication with the tube 102 between the first and second end 103, 104, thereof. The intermediate sensor element 108 may be configured to detect a flow of fluid between the first and second ends 103, 104, of the tube 102 caused by the pressure difference. E.g. if the pressure at the first end 103 is lower than the pressure at the second end 104, then the fluid in the tube 102 may flow from the second end 104 to the first end 103, and in the opposite direction if the pressure is higher at the first end 103. Utilizing the flow of fluid in the tube 102 provides for effectively maintaining a desired pressure control.

The intermediate sensor element 108 may hence be configured to detect the following situations; i) a fluid flow from the first chamber 112 towards the second chamber 113, and/or ii) a fluid flow being below a predefined flow threshold, and/or iii) a fluid flow from the second chamber 113 towards the first chamber 112. Sensor data may be communicated from the sensor element 108 to the control unit 105 for the cases i)-iii) and associated control signals may be sent to the actuator 107 to increase or decrease the distance (d)—i.e. to maintain a desired distance (d)—depending on the sensed fluid flow. The mentioned fluid flow threshold may be construed as a threshold defining a limit of the fluid flow where no compensation of the distance (d) is carried out if the rate of the flow is below the mentioned limit. The intermediate sensor 108 may also have a detection limit, defining a flow threshold to take into account.

The first and second ends 103, 104, of the tube 102 may be configured for connection to respective first 109 and second 110 reference points of the medical device 101 and the patient 201, as schematically illustrated in FIG. 1. A vertical distance (d) between the first and second reference points 109, 110, may thus correspond to said position (d) of the medical device 101 in relation to the patient 201. It is conceivable however that there may be any off-set between the actual positions where the first and second ends 103, 104, are attached and between which positions the distance (d) is measured, e.g. for practicality reasons and depending in the application.

The actuator 107 may be configured to arrange the medical device 101 at a position along a vertical direction 111 in response to the pressure difference, i.e. along the direction 111 as illustrated in FIG. 1. It is conceivable however that the actuator 107 may be configured to manipulate the position of the medical device 101 in three dimensions, including rotating the medical device 101. An angle between the dashed lines indicating the distance (d) in FIG. 1 may accordingly also be varied in case the actuator 107 is configured to rotate the medical device 101 in relation to the patient 201. The position and orientation of the medical device 101 in relation to the patient 201 may accordingly be manipulated in the three dimensional space to compensate for any movement of the patient 201 in this space that may affect the performance of the medical device 101. I.e. any such translatory or tilting movement by the patient 201 may change e.g. fluid dynamics of a fluid communication between the medical device 101 and the patient 201, as exemplified above with respect to the influence of fluid pressure in drainage or infusion applications. The sensor 106 may thus be configured to sense such changes and send the sensor data to the control unit 105 being configured to instruct the actuator 107 to move the medical device 101 in three dimensions (and thereby the first and second ends 103, 104, in relation to each other), to compensate the movement of the patient and restore the desired fluid dynamics.

The control unit 107 may be configured to retrieve sensor data from the sensor 106 at predetermined time intervals, and to send a control signal to the actuator 107 for varying the position (d) of the medical device 101 in response to the sensor data. The time intervals may be set sufficiently short to compensate for sudden changes in the physical position assumed by a human to allow for adjustments of the medical device 101 that are sufficiently responsive to avoid lag which has any negative impact on the patient 201.

As elucidated in the example with respect to FIG. 1 above, the control signal of the control unit 107 may comprise instructions to the actuator 107 to arrange the position (d) so that a vertical distance (d) between the first and second ends 103, 104, is reduced when the aforementioned pressure difference exceeds a predefined pressure threshold. Reducing the distance (d) thus allows for the pressure difference to decrease. Vice versa, the control signal may comprise instructions to the actuator to arrange the position (d) so that a vertical distance (d) between the first and second ends 103, 104, is increased when the pressure difference is below a predefined pressure threshold.

The control signal may comprise instructions to the actuator 107 to arrange the position (d) so that a vertical distance (d) between the first and second ends 103, 104, is kept at a predefined separation to keep the pressure difference at a constant value as the patient 201 moves in relation to the medical device 101. The vertical distance (d) may thus be set to different values depending on the application, to be subsequently maintained by the levelling device 100 as described above.

Further as described in the example above, the first end 103 of the tube 102 may be configured to be connected to a medical device 101 comprising a skull drainage, and the second end 104 of the tube 102 may be configured to be connected to a patient's skull. It is however conceivable that the first and second ends 103, 104, are configured to be connected to various other structures, e.g. infusion devices and to other body parts of the patient 201. Although the examples have primarily discussed medical devices 101 being in fluid communication with the patient 201, where the relative position of the medical device 101 and the patient is of importance, it is also conceivable that the levelling device 100 is used in other applications where it is desired for a medical device 101 to follow the movement of the patient 201. For example, the patient 201 may have different body parts fixed to various support frames to allow healing after a trauma. The medical device 100 may thus comprise such support frame, which may track the position of the patient 201 and thereby increased the freedom of movement, while providing the necessary support. The first end 103 of the tube 102 may thus be attached to the support frame and the second end 104 may be attached to the patient's body part that should be tracked. A defined position (d) between the support frame and the patient's body part is set to a desired value and associated with a corresponding pressure difference between the first and second ends 103, 104. Deviations from this pressure difference, occurring as the patient moves, are detected by the sensor 106, and a compensating control signal is sent to the actuator 107 via the control unit 105 to move the support frame, and thereby maintain the defined position (d) and the associated pressure difference, as described above with respect to the medical device 101.

The sensor 106 may comprise a secondary detector element (not shown) connected to the control unit 107 and being configured to register motion characteristics of the tube 102 such as a velocity or acceleration of a translatory movement or a rotational movement of the tube 102.

The control unit 105 may be configured to control the actuator 107 to adjust a position of the first end 103 relative the second end 104 in dependence on the motion characteristics to maintain a predefined value of the pressure difference. Hence, a secondary detector element may be utilized in combination with the sensor 106 as described above to gather further input concerning the dynamics of the patient's movements in relation to the medical device 101. Motion characteristics such as velocity and acceleration may thus be utilized by the control unit 105 to compensate for the patient's movements in dependence of these characteristics. The corresponding motion characteristics, such as speed and acceleration, of the medical device 101 may thus be varied accordingly to provide for a smooth and accurate tracking of any type of motion.

The first end 103 and/or the second end 104 of the tube 102 may comprise a fixation unit (not shown) configured for removable and non-invasive attachment of the first 103 and/or second end 104 to the patient 201 and/or the medical device 101 at a corresponding reference point 109, 110. The levelling device 100 may thus be configured as an add-on to existing medical systems and procedures.

Figure 2:
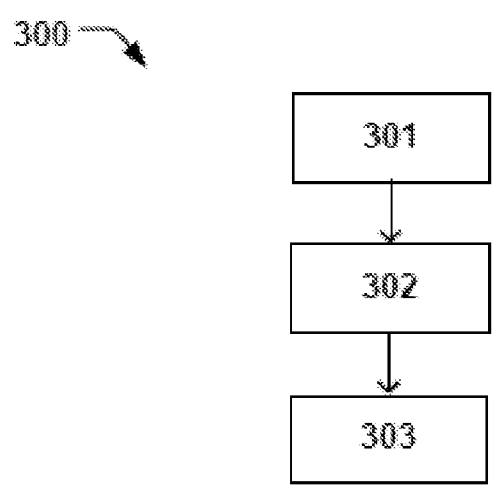
FIG. 2 is a flowchart of a method of controlling the position of a medical device in relation to a patient, according to examples of the disclosure.

FIG. 2 illustrates a flow chart of a method 300 of controlling the position of a medical device in relation to a patient. The order in which the steps of the method 300 are described and illustrated should not be construed as limiting and it is conceivable that the steps can be performed in varying order. The method 300 comprises transmitting 301 sensor data to a control unit 105 which is indicative of a pressure difference between a first and second end 103, 104, of a tube 102 being configured for connection to the medical device 101 and the patient respectively. The first and second ends 103, 104, of the tube 102 are in fluid communication. The method 300 comprises controlling 302 an actuator 107 connected to the control unit 107 and the medical device 101 to arrange 303 a position (d) of the medical device 101 in relation to the patient 201 in dependence on said pressure difference. The method 300 thus provides for the advantageous benefits as described above in relation to the levelling device 100 and FIG. 1.

A computer program product is provided comprising instructions which, when the program is executed by a computer, cause the computer to carry out the steps of the method 300 as described above in relation to FIG. 2.

According to one embodiment, the levelling device 100 may comprise a flexible plastic or polymeric tube 102 which is sealed to prevent liquid or gaseous communication with the external environment. The substantially entire inner volume of the tube 102 may be filled with a liquid, e.g. water or an aqueous salt solution, such as e.g. an aqueous solution of sodium polytungstate. The latter will result in a higher pressure difference between the first 103 and second end 104 of the tube 102 when these ends are located at different vertical planes, as compared to the case of lower density liquids, and thus a higher sensitivity of detection. The sensor 106 may consist of two separate absolute pressure sensors, one being in pressure sensing connection with the liquid in the tube 102 at the first end 103 and the other being in pressure sensing connection with the liquid in the tube 102 at the second end 104. The difference in pressure reading between these two sensors will be positively correlated to the difference in vertical positioning of the first end 103 and the second end 104 and to the density of the pressure communicating liquid within the tube 102. Absolute pressure sensors having suitable electrical output signaling are well known in the art and include, but are not limited to, the low-pressure module MS5536-60 by AMSYS GmbH & Co.

According to one embodiment, the sensor 106 may consist of two separate pressure sensors, e.g absolute pressure sensors, one being in pressure sensing connection with the liquid in the tube 102 at the first end 103 and the other being in pressure sensing connection with the liquid in the tube 102 at the second end 104. The tube 102 may be filled with a liquid, such that e.g. its entire inner volume is occupied by such a liquid without any practically effective amounts of coexisting gaseous volumes. The tube 102 may be sealed to prevent liquid or gaseous communication with the external environment. Advantages of the combination of the features of this embodiment include a minimization of the influence of external factors on the output sensor data. This brings about an advantageous insensitivity towards e.g. variation in internal or external pressure and temperature of the device as such over time, as well as an advantageous insensitivity of e.g. varying external pressure on different parts (e.g. the first and second end of the tube) of the device. In practice, this insensitivity translates into decreased noise and increased long-term stability of the output sensor data, in comparison to a device without the features of this embodiment.

The present invention has been described above with reference to specific examples. However, other examples than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

Itemized List of Embodiments

1. A levelling device (100) for positioning of a medical device (101) in relation to a patient (201) comprising
a tube (102) having fluid communication between a first end (103) and a second end (104), wherein the first end is configured for connection to the medical device and the second end is configured for connection to the patient,
a control unit (105) connected to a sensor (106), wherein the sensor is configured to transmit sensor data to the control unit which is indicative of a pressure difference between the first and second end of the tube,
an actuator (107) connected to the control unit, wherein the actuator is configured to connect to the medical device and to arrange a position (d) of the medical device in relation to the patient in dependence on said pressure difference.

2. Levelling device according to claim 1, wherein the sensor is connected to the first and second end of the tube and is configured to detect the pressure difference therebetween.

3. Levelling device according to claim 2, wherein the first and second ends comprises respective first and second chambers (112, 113) being in fluid communication across the tube, and wherein the sensor is configured to detect the pressure difference between the first and second chambers.

4. Levelling device according to claim 1 or 2, wherein the sensor is connected to an intermediate sensor element (108) positioned in fluid communication with the tube between the first and second end thereof, wherein the intermediate sensor element is configured to detect a flow of fluid between the first and second ends of the tube caused by the pressure difference.

5. Levelling device according to claims 3 and 4, wherein the intermediate sensor element is configured to detect i) a fluid flow from the first chamber towards the second chamber, ii) a fluid flow being below a predefined flow threshold, and iii) a fluid flow from the second chamber towards the first chamber.

6. Levelling device according to any of claims 1-5, wherein the first and second ends of the tube are configured for connection to respective first (109) and second (110) reference points of the medical device and the patient, and wherein a vertical distance between the first and second reference points corresponds to said position of the medical device in relation to the patient.

7. Levelling device according to any of claims 1-6, wherein the actuator is configured to arrange the medical device at a position along a vertical direction (111) in response to the pressure difference.

8. Levelling device according to any of claims 1-7, wherein the control unit is configured to retrieve sensor data from the sensor at predetermined time intervals, and to send a control signal to the actuator for varying said position of the medical device in response to the sensor data.

9. Levelling device according to claim 8, wherein the control signal comprises instructions to said actuator to arrange said position so that a vertical distance (d) between the first and second ends is reduced when said pressure difference exceeds a predefined pressure threshold, and/or wherein control signal comprises instructions to said actuator to arrange said position so that a vertical distance (d) between the first and second ends is increased when said pressure difference is below a predefined pressure threshold.

10. Levelling device according to claim 8 or 9, wherein the control signal comprises instructions to said actuator to arrange said position so that a vertical distance (d) between the first and second ends is kept at a predefined separation to keep said pressure difference at a constant value as the patient moves in relation to the medical device.

11. Levelling device according to any of claims 1-10, wherein the first end of the tube is configured to be connected to a medical device comprising a skull drainage, and wherein the second end of the tube is configured to be connected to a patient's skull.

12. Levelling device according to any of claims 1-11, wherein the sensor comprises a secondary detector element connected to the control unit and being configured to register motion characteristics of the tube such as a velocity or acceleration of a translatory movement or a rotational movement of the tube, and wherein the control unit is configured to control the actuator to adjust a position of the first end relative the second end in dependence on said motion characteristics to maintain a predefined value of said pressure difference.

13. Levelling device according to any of claims 1-12, wherein the first end and/or the second end of the tube comprises a fixation unit configured for removable and non-invasive attachment of the first and/or second end to the patient and/or the medical device at a corresponding reference point (109, 110).

14. Method (300) of controlling the position of a medical device (101) in relation to a patient (201) comprising transmitting (301) sensor data to a control unit (105) which is indicative of a pressure difference between a first and second end (103, 104) of a tube (102) being configured for connection to the medical device and the patient respectively, the first and second ends of the tube being in fluid communication, and controlling (302) an actuator (107) connected to the control unit and the medical device to arrange (303) a position (d) of the medical device in relation to the patient in dependence on said pressure difference.

15. A computer program product comprising instructions which, when the program is executed by a computer, cause the computer to carry out the steps of the method according to claim 14.

The invention claimed is:

1. A levelling device (100) for positioning of a medical device (101) in relation to a patient (201) comprising:
   a tube (102) having fluid communication between a first end (103) and a second end (104), wherein the first end (103) is configured for connection to the medical device (101) and the second end (104) is configured for connection to the said patient (201),
   a control unit (105) connected to a sensor (106), wherein the sensor (106) is configured to transmit sensor data to the control unit (105) which is indicative of a pressure difference between the first and second end (103,104) of the tube (102),
   an actuator (107) connected to the control unit (105), wherein the actuator (107) is configured to connect to the medical device (101) and to arrange a position (d) of the medical device (101) in relation to the patient in dependence on said pressure difference, wherein
   the tube (102) is sealed to prevent liquid or gaseous communication with the external environment;
   the inner volume of the tube (102) is filled with a liquid; and
   the sensor (106) comprises two separate absolute pressure sensors, one being in pressure sensing connection with said liquid in the tube (102) at the first end (103) and the other being in pressure sensing connection with said liquid in the tube (102) at the second end (104).

2. The levelling device (100) according to claim 1, wherein the sensor (106) is configured to detect the pressure difference between said two separate absolute pressure sensors.

3. The levelling device (100) according to claim 1, wherein the sensor (106) is connected to an intermediate sensor element (108) positioned in fluid communication with the tube (102) between the first and second end (103,104) thereof, wherein the intermediate sensor element (108) is configured to detect a flow of fluid between the first and second ends (103,104) of the tube (102) caused by the pressure difference.

4. The levelling device (100) according to claim 1, wherein the first and second ends (103,104) of the tube (102) are configured for connection to respective first (109) and second (110) reference points of the medical device (101) and the patient (201), and wherein a vertical distance between the first and second reference points (109,110) corresponds to said position of the medical device (101) in relation to the patient (201).

5. The levelling device (100) according to claim 1, wherein the actuator (107) is configured to arrange the medical device (101) at a position along a vertical direction (111) in response to the pressure difference.

6. The levelling device (100) according to claim 1, wherein the control unit (105) is configured to retrieve sensor data from the sensor (106) at predetermined time intervals, and to send a control signal to the actuator (107) for varying said position of the medical device (101) in response to the sensor data.

7. The levelling device (100) according to claim 6, wherein the control signal comprises instructions to said actuator (107) to arrange said position so that a vertical distance (d) between the first and second ends (103,104) is reduced when said pressure difference exceeds a predefined pressure threshold, and/or
wherein control signal comprises instructions to said actuator (107) to arrange said position so that a vertical distance (d) between the first and second ends (103, 104) is increased when said pressure difference is below a predefined pressure threshold.

8. The levelling device (100) according to claim 6, wherein the control signal comprises instructions to said actuator (107) to arrange said position so that a vertical distance (d) between the first and second ends (103,104) is kept at a predefined separation to keep said pressure difference at a constant value as the patient moves in relation to the medical device.

9. The levelling device (100) according to claim 1, wherein the first end (103) of the tube (102) is configured to be connected to the medical device comprising a skull drainage, and wherein the second end (104) of the tube (102) is configured to be connected to a patient's skull.

10. The levelling device (100) according to claim 1, wherein the sensor (106) comprises a secondary detector element connected to the control unit (105) and being configured to register motion characteristics of the tube (102) such as a velocity or acceleration of a translatory movement or a rotational movement of the tube, and wherein the control unit (105) is configured to control the actuator (107) to adjust a position of the first end (103) relative the second end (104) in dependence on said motion characteristics to maintain a predefined value of said pressure difference.

11. The levelling device (100) according to claim 1, wherein the first end and/or the second end (103,104) of the tube (102) comprises a fixation unit configured for removable and non-invasive attachment of the first and/or second end (103,104) to the patient (201) and/or the medical device (101) at a corresponding reference point (109, 110).

12. A method (300) of controlling the position of a medical device (101) in relation to a patient (201) comprising:
transmitting (301) sensor data to a control unit (105) which is indicative of a pressure difference between a first and second end (103, 104) of a tube (102) being configured for connection to the medical device (101) and the patient (201) respectively, the first and second ends (103, 104) of the tube (102) being in fluid communication, and
controlling (302) an actuator (107) connected to the control unit (105) and the medical device (101) to arrange (303) a position (d) of the medical device (101) in relation to the patient (201) in dependence on said pressure difference, wherein
the tube (102) is sealed to prevent liquid or gaseous communication with the external environment;
the inner volume of the tube (102) is filled with a liquid; and
the sensor (106) comprises two separate absolute pressure sensors, one being in pressure sensing connection with said liquid in the tube (102) at the first end (103) and the other being in pressure sensing connection with said liquid in the tube (102) at the second end (104).

13. A computer program product comprising instructions which, when the program is executed by a computer, cause the computer to carry out the steps of the method according to claim 12.

* * * * *